United States Patent
Messina et al.

(10) Patent No.: US 10,800,811 B2
(45) Date of Patent: Oct. 13, 2020

(54) PHARMACOLOGICALLY ACTIVE PEPTIDE COMPOUND, PROCESS FOR THE PREPARATION AND USE THEREOF

(71) Applicants: Angela Anna Messina, Catania (IT); Vito Nicola De Pinto, Catania (IT); Andrea Magri', Paternò (IT); Simona Reina, Valverde (IT); Francesca Maria Guarino, Catania (IT); Dipartimento di Scienze Biomediche e Biotecnologiche, Catania (CT) (IT); Dipartimento di Scienze Biologiche, Geologiche e Ambientali, Catania (CT) (IT)

(72) Inventors: Angela Anna Messina, Catania (IT); Vito Nicola De Pinto, Catania (IT); Andrea Magri', Paternò (IT); Simona Reina, Valverde (IT); Francesca Maria Guarino, Catania (IT)

(73) Assignees: Angela Anna Messina, Catania (CT) (IT); Vito Nicola De Pinto, Catania (CT) (IT); Andrea Magri', Paternò (CT) (IT); Simona Reina, Valverde (CT) (IT); Francesca Maria Guarino, Catania (CT) (IT); Dip. di Scienze Biomediche e Biotecnologiche, Catania (CT) (IT); Dip.di Scienze Biologiche, Geologiche e Ambientali, Catania (CT) (IT)

( * ) Notice: Subject to any disclaimer, the term of this patent is extended or adjusted under 35 U.S.C. 154(b) by 0 days.

(21) Appl. No.: 16/084,376

(22) PCT Filed: Mar. 14, 2017

(86) PCT No.: PCT/IB2017/051460
§ 371 (c)(1),
(2) Date: Sep. 12, 2018

(87) PCT Pub. No.: WO2017/158502
PCT Pub. Date: Sep. 21, 2017

(65) Prior Publication Data
US 2019/0071467 A1 Mar. 7, 2019

(30) Foreign Application Priority Data
Mar. 14, 2016 (IT) .............................. UA2016A1610

(51) Int. Cl.
| | |
|---|---|
| A61K 38/00 | (2006.01) |
| C12Q 1/68 | (2018.01) |
| C07K 7/04 | (2006.01) |
| C12N 9/12 | (2006.01) |
| C07K 7/06 | (2006.01) |
| A61P 25/28 | (2006.01) |
| A61P 25/16 | (2006.01) |
| A61P 35/00 | (2006.01) |

(52) U.S. Cl.
CPC ................ *C07K 7/04* (2013.01); *A61P 25/16* (2018.01); *A61P 25/28* (2018.01); *A61P 35/00* (2018.01); *C07K 7/06* (2013.01); *C12N 9/1205* (2013.01); *C12Y 207/01001* (2013.01); *A61K 38/00* (2013.01)

(58) Field of Classification Search
None
See application file for complete search history.

(56) References Cited

U.S. PATENT DOCUMENTS

| | | | | | |
|---|---|---|---|---|---|
| 8,324,175 | B2* | 12/2012 | Ko | ........................ | A61K 31/202 514/23 |
| 8,575,070 | B2* | 11/2013 | Watt | ........................ | C07K 1/047 506/25 |
| 2013/0157925 | A1 | 6/2013 | Ko | | |

OTHER PUBLICATIONS

Shi P. et al., J Alzheimer's Dis (2010) 20 Suppl 2:S311-24.
Shi P. et al., Biochim Biophys Acta (2010) Jan.; 1802(1):45-51.
Tan W et al. Biochim Biophys Acta (2014)1842: 1295-1301 ) p. 3, lines 9-12.
R B. Merrifield, "Solid Phase Peptide Synthesis. The Synthesis of a Tetrapeptide", Journal of the American Chemical Society, 1963, 85 (14): 2149, doi:l 0.1021/ja00897a025 See p. 10, lines 10-13.
Tomasello F. et al., "The voltage-dependent anion selective channel 1 (VDAC 1) topography in the mitochondrial outer membrane as detected in intact cell. PLoS One 2013; 8:e81522". See p. 16, lines 14-16.
Cashman NR et al. "Neuroblastoma x spinal cord (NSC) 20 hybrid cell lines resemble developing motor neurons". Dev. Dyn. (1992) 194:209-21.
Durham HD et al., "Evaluation of the spinal cord neuron X neuroblastoma hybrid cell line NSC-34 as a model for neurotoxicity testing. Neurotoxicology" (1993) 14:387-395. See p. 17, lines 19-23.
Checchetto V. et al., "Recombinant human Voltage Dependent Anion selective Channel isoform 3 (h VDAC3) forms pores with a very small conductance". Cell Physiol Biochem (2014) 34(3): 842-853. See p. 18, lines 13-15.
Israelson A. et al., "Misfolded Mutant SODI Directly Inhibits VDACI Conductance in a Mouse Model of Inherited ALS". Neuron (2010) Aug. 26; 67(4):575-587. See p. 19, lines 2-4.
Ben-Hail D, Shoshan-Barmatz V. "Reconstitution of purified VDAC 1 into a lipid bilayer and recording of channel conductance". Cold Spring Harb Protoc. Jan. 1, 2014;2014(1):100-5. doi: 10.1101/pdb. prot073148. PubMed PMID: 24371316 See p. 19, lines 22-25.

(Continued)

*Primary Examiner* — Olga N Chernyshev
(74) *Attorney, Agent, or Firm* — Silvia Salvadori (57) ABSTRACT

Object of the invention is a synthetic peptide, in particular a synthetic peptide to be used as medicament, in particular to be used in the treatment of neurodegenerative diseases and Amyotrophic Lateral Sclerosis (ALS), and compositions comprising such synthetic peptide. Furthermore, the invention concerns processes for the preparation of said synthetic peptide.

4 Claims, 6 Drawing Sheets
Specification includes a Sequence Listing.

(56) References Cited

OTHER PUBLICATIONS

Mosmann T., "Rapid colorimetric assay for cellular growth and survival: application to proliferation and cytotoxicity assays". J Immunol Methods (1983) 65:55-63. See p. 22, lines 5-7.

Sanchez NS and K, Nigsberg M. "Using Yeast to Easily Determine Mitochondrial Functionality with 1-(4,5-Dimethylthiazol-2-yl)-3,5-diphenyltetrazolium Bromide (MTT) Assay". Biochem Mol Biol Educ (2006) 34(3)209-212.

Kaneko I., Yamada N., Sakuraba Y. et al. "Suppression of mitochondrial succinate dehydrogenase, a primary target of beta-amyloid, and its derivative racemized at Ser residue." J Neurochem (1995) 65(6):2585-93. See p. 24, lines 4-9.

International Search Report and written opinion issued by the EPO for PCT/IB2017/051460 dated May 29, 2917.

European Search Report issued by the EPO for Italian priority application No. UA 20161610.

\* cited by examiner

PHARMACOLOGICALLY ACTIVE PEPTIDE COMPOUND, PROCESS FOR THE PREPARATION AND USE THEREOF

RELATED APPLICATIONS

This application is a US national phase application of international application number PCT/IB2017/051460, filed 14 Mar. 2017, which designates the US and claims priority to Italian application UA2016A001610 filed 14 Mar. 2016, the contents of each of which are hereby incorporated by reference as if set forth in their entireties.

SUMMARY OF THE INVENTION

Object of the invention is a pharmacologically active peptide compound, in particular a synthetic peptide to be used as medicament and compositions comprising said synthetic peptide. Furthermore the invention concerns processes for the production of such synthetic peptide.

TECHNICAL BACKGROUND OF THE INVENTION

Neurodegenerative pathologies are a wide number of central nervous system (CNS) disorders, showing as a common trait a chronic and selective degeneration and death of the neuronal cell.

Among the neurodegenerative diseases, Amyotrophic Lateral Sclerosis (ALS), also known as "Lou Gehrig disease", "Charcoat disease" or "Motor Neuron disease", is the commonest motor neuron disease arising in adults. ALS is a progressive neurodegenerative disease that causes the degeneration and death of motor neurons, i.e. brain nervous cells and spinal cord cells which control voluntary muscles. The progression of the illness varies from patient to patient, with invariably severe effects on the life quality and life expectation for the patient. The patient will progressively and irreversibly loose normal swallowing (dysphagia), wording (dysarthria), control of skeletal muscle and a paralysis with variable extension, arriving to the block of respiratory muscles which consequently requires artificial respiration and causes the final exitus.

In the last 30 years, the incidence (i.e. the number of new diagnosed cases) of ALS has raised. The incidence rate is now considered of 2-4 cases per 100,000 person/year and the prevalence, in western countries, is 10 cases per 100,000 person. In Italy there are at present 6,000 patients.

The causes of the disease are unknown; however it is widely accepted that ALS is a multi-factorial disease. Genetic factors have an important role in ALS: there are more than 30 genes, whose mutations have been associated with the disease. Other environmental factors and life-style behaviors are suspected to add risk factors to the disease onset.

It is known that mutations in the sod1 gene, mapping to chromosome 21q22, are associated with about 10% of ALS cases. The human sod1 gene encodes the enzyme superoxide dismutase-1, hSOD1, (EC 1-15-1-1, OMIM #147450). SOD1 is a major cytoplasmic antioxidant enzyme, ubiquitariously expressed in the organism and member of the oxidoreductase enzymes. The physiological role of SOD1 in various cell compartments is to metabolize superoxide radicals ($O_2^-$), produced by various pathways, to molecular oxygen ($O_2$) and hydrogen peroxide ($H_2O_2$), thus providing a defense against anion superoxide toxicity.

More than 160 point mutations in the sod1 gene have been associated with ALS and at least 5 different inheritage lineages have been outlined. The most widely accepted mechanism of mutated SOD1 toxicity is linked to the enzyme misfolding (i.e. an erroneous folding of the newly synthesized protein), leading to accumulation of insoluble aggregates in the motor neurons. The protein aggregates bodies, during the disease, progressively accumulates in the motor neurons cytosol causing, at the end, the cell death. This pathogenic mechanism found in ALS is similar to what was found in other neurodegenerative diseases. Also in transgenic mice expressing mutated SOD1 a similar protein aggregation in motor neurons has been described, and this leads to a ALS-like syndrome: for this reason such mutated SOD1 mice strains are widely accepted as animal models of ALS. In particular, the transgenic mouse overexpressing the G93A mutantSOD1 (SOD1-G93A) is the ALS animal model most utilized in therapeutical targeted drug screenings.

The molecular pathways involved in pathophysiology of ALS are various as, for example: aggregation of misfolded proteins, mitochondrial dysfunction, excitotocity, apoptosis, autophagy, oxidative stress, altered axonal transport, RNA synthesis regulation and editing. One of the most central hub of the disease at cellular level is mitochondrial dysfunction, since mitochondria are crucial entities in the energetic production, in the metabolism, in $Ca^{2+}$ homeostasis and signaling, in the network of apoptotic decision-makers. Accordingly, it is well established that mitochondria damages are among the prominent causes of neurodegeneration, including ALS, Parkinson's and Alzheimer's diseases. It has been found, indeed, that mitochondria degeneration is a precocious symptom in motor neurons degeneration, appearing much earlier than clinical symptoms.

Mutant SOD1 molecules, due to their misfolding propensity, can easily aggregate to form insoluble bodies that associate to the cytoplasmic side of the outer mitochondrial membrane (OMM). This phenomenon is specific for motor neurons. The mutant SOD1 protein aggregates clog the permeability of the membrane, blocking the normal exchange of ions and metabolites between the two sides of the membrane: this accumulation, in turn, impacts on the normal bioenergetics features of the organelle and causes its dysfunction and degeneration (Shi P. et al., J Alzheimer's Dis (2010) 20 Suppl 2:S311-24; Shi P. et al., Biochim Biophys Acta (2010) January; 1802(1):45-51; Tan W et al. Biochim Biophys Acta (2014) 1842:1295-1301).

It is known that mutant SOD1, but not the wild type (i.e. not mutant) SOD1 (SOD1WT), binds to VDAC1, a main protein located in the OMM. VDACs are transmembrane pore-forming proteins of the OMM, with the essential role of allowing the permeability of the membrane to small metabolites, nucleotides, ions, water. In studies that characterized the interaction between the OMM and the mutated SOD1, or between VDAC1 and mutated SOD1, it was found that mutated SOD1 specifically binds VDAC1 in spinal cord, but not in other neurological districts, like brain, in ALS mouse. Furthermore, a direct influence on the conductance ability of VDAC1 was shown in in vitro systems in the presence of mutated SOD1, confirming the binding of the enzyme to the channel protein. This binding is specific of the mutated SOD1, since the wt SOD1 cannot exhert the same inhibition. It is an effect present at a pre-symptomatic stage of the disease. The mutant SOD1 inhibition of VDAC1 conductance has the same size of the inhibition resulting from the complete deletion of vdac1 gene.

The inactivation of vdac1 gene accelerates the onset of the disease, reducing by two months the survival of ALS mouse SOD1G37R/VDAC1+/−, a mouse expressing the SOD1 carrying the mutation G37R together with an heterozygous form of VDAC1, and of ALS mice SOD1G37R/VDAC1−/−, a mouse completely lacking any expression of VDAC1.

Nowadays no therapy against ALS exists.

Some molecules proposed to be potential therapeutical agents against ALS are presently under study, but they show relevant drawbacks, together with favorable activities.

Dexpramipexole, for instance, a drug used in Parkinson's disease, has been used to counteract mitochondrial dysfunction and oxidative stress. Nevertheless, clinical trials showed that Dexpramipexole lacks any efficacy in ALS patients, and it is even ineffective to slow the disease and give relief to any symptom. Similar unsuccessful results have been showed with other molecules like oleoxime and creatine, used as mitochondrial function stimulators.

In addition to metabolic derangement also neuroinflammation looks to play a prevalent role in ALS (and other neurodegenerative diseases) etiology. It has been indeed found in brain and spinal cord of ALS patients the advanced inflammation of microglia and the presence of blood-derived immune cells. These cells are stimulated to release cytotoxic molecules, involved in motor neuron death. Also macrophages can damage motor neurons upon their invasion of the NCS where they can also release toxic molecules. Macrophages can further recruit T CD4 lymphocytes, drivers of an immune reaction mediated by B and CD8 lymphocytes towards neurons. There are presently running several clinical or pre-clinical trials with molecules aiming to T lymphocytes, microglia or macrophages. Among them, Fingolimid, a drug approved for the therapy of multiple sclerosis (MS), does not show any activity in ALS. Other drugs with similar activity against T lymphocytes are CDP7657 (a modulator of T-cell, anti-CD40L) and Tocilizumab, a biological drug approved for rheumatoid arthritis: they show conflicting results in the sporadic form of ALS (sALS). Another example is NP001, reducing macrophages activation, and Lithium carbonate, a classical inorganic compound, used against bipolar disorders and depression, whose utilization in ALS has been found to have no influence on disease progression and survival. Masitinib (a kinase inhibitor targeting the cKIT receptor of staminal cell factor (CSF), used to stop cytokine production and mast cells migration) and Fasudil hydrochloride (inhibitor of ROCK, Rho associated protein kinase, proved to reduce astroglial and microglial cell migration to spinal cord) have been used to treat inflammatory disease including MS but proved to be inefficacy in ALS. GSK2606414 (an inhibitor of PERK, Protein kinase R-like kinase, and consequently of neuronal death through inhibition of TDP43 accumulation), Kenapullone (inhibitor of several cyclin-dependent kinases like GSK3 □ □ a glycogen synthase kinase reducing the neuron apoptosis and accumulation of mutated SOD1), Neurimmune NI204 (a MAb to misfolded SOD1 accumulation in motor neurons) are also under investigation for ALS.

In another class of molecules it has been proposed that SOD1RX, an antisense RNA targeting the mutated SOD1 mRNA, and C9orf72, an antisense oligonucleotide against sequence repeats in C9ORF72 gene, could be used in ALS to reduce the accumulation of misfolded proteins. These compounds, however, present heavy limitations, since they cannot work on very short repetitions or, unfortunately, they do not show any productive result in reducing the target gene expression levels. Other compounds to be tested are Nuedexta (it targets the sigma I receptor of neurons), and GM604, a molecule regulator, both supposed to protect neurons.

A considerable attention is nowadays devoted to cell therapy. One of the strategy of these therapies is to substitute toxic astrocytes by a transplant of normal astrocytes or neural staminal cells (NSC). In this kind of treatment the injection into the spinal cord of fibroblast-differentiated astrocytes or even human embryo derived astrocytes is expected. Results form experimental co-cultures of motor neurons together with astrocytes differentiated from ALS patients skin fibroblasts suggest that toxic astrocytes can be lethal only in some sporadic form of ALS. The envisaged cell therapies can be very complicate and exceedingly expensive. The clinical trials of NSC therapies suggest a potential active role of anti-rejection drugs used thorough the therapy. Also immunosuppressors are thus under investigation for ALS treatment. Unfortunately these last compounds appear not to be very well tolerated by patients.

Other patho-ethiogenic mechanisms are under investigation as possible therapeutical target in ALS and more clinical pre-trials or trials have been underwent. The efficacy of Ozanezumab in fighting degeneration of neuro-muscle junction in ALS has been begun. Ozanezumab is a monoclonal antibody targeting NOGO-A, a protein that contrasts axon growth and whose expression has been found enhanced in ALS.

Other molecules are under consideration because they could improve the life-conditions or the survival expectation of patients. This is believed to be reached through a direct or indirect improvement of neurons health. Some molecules appear to limit additional damages to neurons, slowing in this way the disease progression. Mexitilene acts inhibiting the Sodium channel and in this way reducing its hyperexcitation. Tirasemvit is a selective activator of troponin and modulator of skeletal muscle contractility, thus able to improve the calcium sensitivity. It was thus proposed that Tirasemvit could improve the strength of several skeletal muscles, in particular those responsible of the respiration: unfortunately the experiments on ALS model mice did not confirm such ability.

The only medicament against ALS approved, until now, by Food and Drug Administration (FDA) is Riluzole, whose administration is able to extend life expectation of only few months, without any effect on the skeletal muscle strength loss. It is probable that Riluzole decreases glutamate release: glutamate overload is one of the mechanisms of motor neuron degeneration. Unfortunately statistical analysis showed that the best result of Riluzole administration is the poor extension of life expectation of about three months.

In general, it is possible to conclude that nowadays very few, if any, clinical trials with reasonable probability of impact on ALS are underway. An urgent need of new strategies and new therapeutic approaches to develop therapeutical actions against ALS and, in general, neurodegenerative diseases is thus a responsibility for the scientific community.

OBJECTS OF THE INVENTION

Object of the present invention is to provide a pharmacologically active compound to treat amyotrophic lateral sclerosis (ALS) and, in general, neurodegenerative diseases raising in the adult age like Parkinson's (PD) and Alzheimer's disease (AD).

Object of the present invention is also to provide a pharmacologically active compound effective to improve life expectation of patients suffering for neurodegenerative diseases, in particular ALS.

Also object of the present invention is to provide a pharmacologically active compound effective in reducing symptoms in patients suffering for neurodegenerative diseases, in particular ALS.

Still another object of the present invention is to provide a pharmacologically active compound effective in slowing down the disease progression in patients suffering for neurodegenerative diseases, in particular ALS.

Still another object of the present invention is to provide a pharmacologically active compound effective in neurodegenerative diseases, in particular ALS, whose production is simple, fast and economical.

DESCRIPTION OF THE INVENTION

These and other objects which will be specified in more detail in the following description are obtained by a pharmaceutically active peptide compound, in particular, the synthetic peptide of sequence IAAQLLAYYFT (SEQ. ID NO. 1).

Preferably, the synthetic peptide of the present invention has an amino acid sequence having at least 70%, preferably at least 80%, more preferably at least 90% sequence identity or homology to the sequence IAAQLLAYYFT (SEQ. ID NO. 1).

In a particularly preferred embodiment of the invention, said synthetic peptide has a sequence identity with the sequence IAAQLLAYYFT (SEQ. ID NO. 1) comprised between 95 and 99%.

It has been surprisingly observed in the invention, indeed, that the peptide with the sequence IAAQLLAYYFT (SEQ. ID NO. 1), also called "NHK1", is able to counteract the binding between the mitochondrial protein VDAC1 and mutant forms of SOD1, preventing the mitochondrial degeneration associated with the VDAC1-mutSOD1 binding, and consequently the raise of ALS or other neurodegenerative diseases like Parkinson (PD) and Alzheimer (AD).

It has been indeed found that the synthetic peptide with amino acid sequence IAAQLLAYYFT (SEQ. ID NO. 1) according to the invention and its above-defined homologous, is able to hinder the interaction between mutated SOD1 and VDAC1, and it is able to counteract the loss of viability of cells where mitochondrial function has been damaged by the mutated forms of SOD1 and by the binding of these mutant molecules to VDAC1.

In an embodiment of this invention, the synthetic peptide is characterized by having a length between 11 and 21 amino acids, preferably between 11 and 15 amino acids. When the peptide, according to the present invention, is 21 amino acids long, its sequence is the following: MIAAQLLAYYFTELKDDQVKK (SEQ. ID NO. 9). When the peptide, according to the present invention, is 15 amino acids long, its sequence is the following: MIAAQLLAYYFTELK (SEQ. ID NO. 10). In these descriptions, the amino acid sequences are reported in the direction from the N-terminus towards the C-terminus; for example, in the sequence IAAQLLAYYFT (SEQ. ID NO. 1), the residue "I" (Isoleucine) is the N-terminal residue, while the residue "T" (Threonine) is the C-terminal residue.

In an embodiment of this invention, in a process for the synthesis, the synthetic peptide is labeled with a detectable probe.

It is considered a "detectable probe" a molecule that can be detected and localized with available techniques; as an example there are emitting radioisotopes, fluorophores (proteic and not-proteic) and protein tags. These detectable probes are especially useful because they allow to locate with specificity, precision and ease the peptide to which are bound, allowing a simpler purification and/or making simpler their study both in vitro and in vivo.

In a cell, for example, the detectable probe will allow, according to the invention, to "track" the synthetic peptide with available techniques. In a preferred embodiment of the invention, the synthetic peptide is bound with a detectable probe chosen among a HA-tag (HemoAgglutinin-tag), biotin and fluorescein isothiocyanate (FITC).

Object of the present invention also concerns the process for the peptide synthesis according to the invention, i.e. with the sequence IAAQLLAYYFT (SEQ. ID NO. 1): such a method will utilize at least one elongation step in the direction from the C-terminus towards the N-terminus. For the sake of clarity, the synthetic process will be named in the following text as "chemical method" or "chemical synthesis".

In the chemical method, the synthesis of the synthetic peptide is carried out from the C-terminus towards the N-terminus, i.e. in the opposite direction as the ribosomal synthesis that instead is carried out from the N-terminus towards the C-terminus. According to the present invention, the chemical synthesis from the C-terminus towards the N-terminus will follow the following steps:

1) binding of the first amino acid to a solid support; the preferred binding to the solid support will be by the α-carboxylic group of the first amino acid;
2) elongation of the peptide from the C-terminus towards the N-terminus, by the formation of a covalent bond between the α-carboxylic group of each added amino acid with the α-amino group of the amino acid which precedes and thus forms the N-terminus of the growing peptide; and
3) detachment of the synthetic peptide from the solid support.

At the end, the amino acid bound to the solid support in phase 1) will be the C-terminal residue of the synthetic peptide, at the end of the synthesis.

As an example according to a preferred embodiment, the chemical synthesis of the synthetic peptide from the C-terminus towards the N-terminus, in the present invention, will follow the following steps:

1) binding of the first amino acid to a solid support; the preferred binding to the solid support will be by the α-carboxylic group of the amino acid;
2a) binding of a second amino acid to the first amino acid with the formation of a peptide bond between the second and the first amino acid; in other words, the α-carboxylic group of the second amino acid forms a covalent bond with the α-amino group of the first amino acid;
2b) sequential addition of amino acids following the second one: the α-carboxylic group of each amino acid forms a covalent bond with the α-amino group of the preceding amino acid;
3) detachment of the synthesized peptide from the solid support.

In this last example, the elongation in direction from the C-terminus towards the N-terminus comprises the steps 2a) and 2b) as above outlined; the steps 2a) and 2b) are cyclically repeated for each amino acid following the first one (bound to the solid support), until the programmed amino acid sequence is obtained.

The preferred solid support to be used in the chemical method producing the synthesis of the synthetic peptide from the C-terminus towards the N-terminus in the present invention are inert polymeric resins.

Examples of preferred resins are 2-Chlorotrityl chloride (Cl resin) or, in general, polystyrene- or PEG, or polyacrylamide-based resins.

Preferably, the amino acids utilized in the synthetic method directed from the C-terminus towards the N-terminus have the N-terminal α-amino group protected by a covalent bound group. In this occurrence the protecting group can be next removed, allowing the reaction with the following amino acid. The preferred reaction expects that the protecting group is removed from the amino acid soon after such amino acid is bound to the preceding residue in the peptide to be synthesized.

The preferred examples of protecting groups are: 9-Fluorenylmethyloxycarbonyl (Fmoc) or tert-Butyloxycarbonyl (t-Boc). The preferred synthetic process of the peptide according to the invention is the solid phase peptide synthetic method (SPPS) (R. B. Merrifield, "Solid Phase Peptide Synthesis. The Synthesis of a Tetrapeptide", Journal of the American Chemical Society, 1963, 85 (14): 2149, doi: 10.1021/ja00897a025).

Still object of present invention is a process of the synthesis of the peptide compound of sequence IAAQLLAYYFT (SEQ. ID NO. 1): said preferred process comprising at least one step where at least one expression vector comprising a nucleotide sequence encoding the synthetic peptide with the sequence IAAQLLAYYFT (SEQ. ID NO. 1) is inserted in at least one cell. This method will be named in the following text "biotechnological process" or "biotechnological synthesis".

Preferred cells to be utilized in the "biotechnological synthesis" of the peptide according to the invention are chosen among eukaryotic and/or prokaryotic cells, in particular are preferred eukaryotic cells.

The foreseen preferred biotechnological synthesis, comprises at least one step of transfection of eukaryotic cells with at least one expression vector comprising a nucleotide sequence coding for said synthetic peptide.

It is preferred that eukaryotic cells are mammalian cells.

It is preferred that eukaryotic cells are from stable cell lines, as an example HeLa, NSC34, SH-SY5Y, HEK293 cells; as an alternative, also iPSC cells can be used. iPSC cells are provided starting from adult human cell re-programmed to stem cell and induced to motor neurons. Also iPS, i.e. induced pluripotent stem cells, can be used. iPS cells are a useful disease model because they are obtained from patients and thus carry themselves one or more genetic mutations associated with the disease. According to the present invention, the expression vector can be any vector, of whatsoever origin, useful for the gene cloning. Expression vectors according to the invention are plasmidic and viral vectors. The preferred expression vector is a plasmidic vector.

When the synthetic peptide has the sequence IAAQLLYYFT (SEQ. ID NO. 1), the expression vector comprises at least the nucleotide sequence coding the peptide with amino acid sequence IAAQLLYYFT (SEQ. ID NO. 1).

The preferred nucleotide sequence coding the peptide with amino acid sequence IAAQLLYYFT (SEQ. ID NO. 1) is: 5'-ATCGCCGCGAGCTCCTGGCCTATTACT-TCACGTGA-3' (SEQ. ID NO. 2).

Since the genetic code is degenerated, other nucleotide sequences, different from SEQ. ID NO. 2 can be equally utilized to code the sequence IAAQLLAYYFT (SEQ. ID NO. 1).

Preferably, the insertion of at least one expression vector comprising a nucleotide sequence coding the synthetic peptide in at least one cell, preferably a eukaryotic cell, is carried out with known techniques.

Further object of the invention is a pharmaceutical composition comprising at least a synthetic peptide with the sequence IAAQLLAYYFT (SEQ. ID NO. 1).

Preferably, the pharmaceutical composition of the present invention comprises other bulking and/or additive agents commonly used in pharmaceutical technology.

The present invention also concerns the synthetic peptide IAAQLLAYYFT (SEQ. ID NO. 1) to be used as a medicament (drug).

The present invention also concerns the synthetic peptide IAAQLLAYYFT (SEQ. ID NO. 1) to be used as in treatment of amyotrophic lateral sclerosis (ALS) or, in general, of neurodegenerative diseases like Parkinson's or Alzheimer's diseases.

As previously reported, in particular, the said synthetic peptide, that is the object of the present invention, showed a surprising efficacy in counteracting the binding between the mitochondrial protein VDAC1 and mutated forms of the protein SOD1, preventing the mitochondrial degeneration due to the interactions between these two proteins.

As a consequence, the synthetic peptide of the present invention can be advantageously applied in the treatment of amyotrophic lateral sclerosis (ALS). The present invention thus refers to a synthetic peptide with the sequence IAAQLLAYYFT (SEQ. ID NO. 1) to be used as a medicament (drug) for treating neurodegenerative diseases, preferably in ALS.

The present invention also concerns the synthetic peptide IAAQLLAYYFT (SEQ. ID NO. 1) to be used as in treatment of neurodegenerative diseases like Parkinson's or Alzheimer's diseases.

As previously reported, in particular, the said synthetic peptide, that is the object of the present invention, showed a surprising efficacy in protecting mitochondria, preventing the mitochondrial degeneration, involved in several neurodegenerative diseases like, for example, ALS, Parkinson's or Alzheimer's diseases.

The present invention also concerns the synthetic peptide IAAQLLAYYFT (SEQ. ID NO. 1) to be used in cancer treatment.

As previously reported, in particular, the synthetic peptide that is the object of the present invention showed a surprising interaction with the mitochondrial protein VDAC1 that is able to produce a pro-apoptotic effect in tumor cell, causing the cell death of tumor cells and thus blocking their proliferation.

Further object of the invention is a pharmaceutical mixture to be used as a medicament (drug), comprising the synthetic peptide of the present invention.

Likewise, an object of the present invention is the pharmaceutical composition comprising the synthetic peptide of the present invention, to be used as a medicament (drug) to treat neurodegenerative diseases, in particular to treat ALS.

The present invention also concerns the pharmaceutical composition comprising the synthetic peptide of the present invention, to be used as a medicament (drug) in cancer treatment.

The present invention will be described in detail with reference to the following experimental part, only as an explicative aim, but not limited to it.

The experimental results are detailed in the attached Figures.

EXPERIMENTAL SECTION

Experiment 1—Synthesis of Synthetic Peptide NHK1 (Method)

Experiment 1A—Chemical Synthesis of Synthetic Peptide NHK1

The synthetic peptide NHK1 of the present invention, with sequence $NH_2$-IAAQLLAYYFT-COOH (SEQ. ID NO. 1), or Isoleucine-Alanine-Alanine-Glutamine-Leucine-Leucine-Alanine-Tyrosine-Tyrosine-Phenylalanine-Threonine, molecular weight 1,273.42, pI=5.50, has been synthesized by the standard chemical method of solid phase peptide synthesis (SPPS) in an automated synthesizer. At a variance from the natural synthesis in ribosome, the SPPS synthesizes the peptide in the direction from the C-terminus towards the N-terminus. Therefore, the synthesis of NHK1 peptide occurs from the C-terminal amino acid Threonine (Thr or T) towards the N-terminal amino acid Isoleucine (Ile or I). The N-terminal of each amino acid to be added in the sequence is protected by the 9-Fluorenylmethyloxycarbonyl group (Fmoc). The peptide bond is formed between the N-terminal amino group of the peptide immobilized through its C-terminus to the solid phase (an insoluble resin) and the entering amino acid, whose N-terminal is protected by a Fmoc group. In the next step the Fmoc group is cleaved and the amino acid is deprotected and the new N-terminus becomes available for binding a new amino acid. For this reason, after each reaction, many washing steps with appropriate solvents are performed, aiming to completely remove reagents from the liquid phase and bioproducts of the coupling phase, while the growing peptide is covalently bound to the insoluble resin.

The SPPS is thus a cyclic process of repeated reactions in which: the amino acid bound to the growing peptide is deprotected—washing steps—addition and reaction of the entering (next) amino acid with the deprotected amino acid and elongation of the growing peptide by the new amino acid—washing steps.

These were the technical steps of SPPS synthesis of said peptide NHK1:

i) binding of the first Fmoc-protected amino acid (Fmoc-Threonine) to the 2-Chlorotrityl chloride resin (Cl-resin): the reagents used as activators of the amino acid coupling are Diisopropylcarbodiimide (DIC) e 1-Hydroxybenzotriazole (HOBt);

ii) deprotection of Fmoc group by 25% piperidine in N,N-Dimethylformamide (DMF);

iii) neutralization of the exposed amino group;

iv) binding of the next Fmoc-protected amino acid (Fmoc-AA) as in i). There is an exception: the peptide sequence—QLL (SEQ. ID NO. 11) requires the activation of the coupling reaction by N,N-Diisopropylethylamine (DIEA) and N-[(Dimethylamino)-1H-1,2,3-triazolo[4,5-b]pyridin-1-ylmethylene]-N methylmethanaminium hexafluorophosphate N-oxide (HATU), due to synthesis problems;

v) release of the Fmoc group;

vi) release of the peptide from the binding resin by trifluoroacetic acid (TFA) and deprotection of the lateral residues, also blocked.

Steps ii) to iv) are repeated as a cycle for each new amino acid introduced in the sequence. Steps v) and vi) are the final steps of the peptide synthesis, performed once the desired sequence is accomplished.

Step iii) neutralization of amino groups is carried on with triethylamine, preferably.

Neutralization of amino group transforms the protonated amine in a free amine, thus nucleophile, and able to attack the symmetric anhydride in the next reaction (step iv). In this way the synthetic peptide named NHK1, object of the present invention, with the sequence IAAQLLAYYFT (SEQ. Id NO. 1) was obtained.

Experiment 1B—Biotechnological Synthesis of Synthetic Peptide NHK1 by Expression in Mammalian Cell The said peptide NHK1, object of the present invention, with the sequence IAAQLLAYYFT (SEQ. Id NO. 1) was produced by expressing a plasmidic vector comprising the nucleotide sequence 5'-ATCGCCGCGCAGCTCCTGGC-CTATTACTTCACGTGA-3' (Seq. Id NO. 2) under the control of an eukaryotic promoter, in stable cell lines (in particular the stable cell lines HeLa and NSC-34).

In the first step two complementary oligonucleotides with the following sequences have been chemically synthesized:

(Seq. Id NO. 3)
5'-<u>CTAG</u>CATGATCGCCGCGCAGCTCCTGGCCTATTACTTCACGTGA<u>G</u>-3';

(Seq. Id NO. 4)
3'-<u>G</u>TACTAGCGGCGCGTCGAGGACCGGATAATGAAGTGCACT<u>CAGC T</u>-5'.

The oligonucleotides contain sequences compatible with restriction sites NdeI and SalI (underscored). The annealing between these two oligonucleotide sequences yielded a double strand DNA (dsDNA-NHK1) containing the sequence coding for the peptide NHK1 of the present invention, flanked by single strand sequences corresponding, respectively, to those obtained upon digestion of restriction sites NdeI and SalI.

Next, the sequence dsDNA-NHK1 was cloned in a plasmidic expression vector for eukaryotic cells pCMSmtRed, a modified pCMS-eGFP (Clontech), whose eGFP transfection marker was substituted with the Red Fluorescent Protein (RFP) sequence from *Discosoma* spp fused after the mitochondrial targeting sequence obtained from human Cytochrome c oxidase subunit VIII gene; this sequence expresses the fluorescent protein to the mitochondria and is a transfection marker [Tomasello F. et al., The voltage-dependent anion selective channel 1 (VDAC1) topography in the mitochondrial outer membrane as detected in intact cell. PLoS One 2013; 8:e81522.]. This construct has been named pCMSmtRed-NHK1.

In addition, a further version of the said peptide NHK1 object of the invention, carrying fused at its C-terminus the HemoAgglutinin sequence (HA-tag) (NHK1-HA) was produced. The HA sequence used as a tag, corresponds to the amino acid sequence 98-106 of the influenza virus HemoAgglutinin, a glycoprotein located on the virus surface and required for the viral infection. The nucleotide sequence of HA-tag is the following: 5'-TACCCATACGATGTTCCA-GATTACGCT-3' (SEQ. Id NO. 5); the corresponding amino acid sequence is the following: YPYDVPDYA (SEQ. Id NO. 6) (the amino acid sequence is in direction from the N-terminus (residue Y) towards the C-terminus (residue A)). It is well established that the addition of HA tag does not produce any interference with the activity or the targeting of the protein to which it is fused.

To provide the fusion protein NHK1-HA, a second pair of complementary oligonucleotides corresponding to the dsDNA coding the sequence NHK1 fused at its C-terminus with the sequence HA was synthesized. This dsDNA contain restriction sites NdeI and SalI, respectively, one at each extremity:

(SEQ. Id NO. 7)
5'<u>CTAG</u>CATGATCGCCGCGCAGCTCCTGGCCTATTACTTCACGTGATACC CATACGATGTTCCAGATTACGCT<u>G</u>-3'

(SEQ. Id NO. 8)
3'<u>G</u>TACTAGCGGCGCGTCGAGGACCGGATAATGAAGTGCACTATGGGTAT GCTACAAGGTCTAATGCGA<u>CAGCT</u>-5'.

The oligonucleotides contain sequences compatible with restriction sites NdeI and SalI (underscored) and the sequence coding for HA tag (bold).

The annealing between these two oligonucleotide sequences yielded a double strand DNA (dsDNA-NHK1-HA). The sequence dsDNA-NHK1-HA was cloned at restriction sites NdeI and SalI of the plasmidic expression vector pCMS-mtDsRed and this construct was named pCMS-mtDsRed-NHK1-HA.

The action of the said NHK1 peptide upon the complex VDAC1/SOD1-G93A, i.e. the complex formed by the interaction between protein VDAC1 and the mutant enzyme SOD1 (exactly the mutant G93A, where the glycine 93 was replaced by alanine) was evaluated by in vitro and in cellulo experiments, i.e. in the NSC34 cell line. NSC34 is a hybrid cell line obtained by fusing mice motor neurons with neuroblastoma cells. The NSC34 cell line is widely recognized as cell model of motor neurons and, following its transfection with mutated SOD1, it is considered a reference model of ALS [Cashman N R et al. Neuroblastoma×spinal cord (NSC) hybrid cell lines resemble developing motor neurons. Dev. Dyn. (1992) 194:209-21; Durham H D et al., Evaluation of the spinal cord neuron×neuroblastoma hybrid cell line NSC-34 as a model for neurotoxicity testing. Neurotoxicology (1993) 14:387-395.].

Experiment 2—Production and Purification of VDAC1, SOD1-G93A, SOD1WT

In in vitro experiments, the action of the peptide NHK1 has been directly assayed in test tubes against the complex VDAC1/SOD1-G93A formed by the interaction of recombinant and purified proteins. The human proteins VDAC1, SOD1-G93A and SOD1WT were preliminarily produced and purified. Human SOD1 (both mutant and wt) and human VDAC1 were expressed in *Escherichia coli* BL21 (DE3) fused at the C-terminus with the Strep-tag (SOD1-G93A and SOD1WT) or His-tag (VDAC1). Human SOD1 (both mutant SOD1 and SOD1WT, Gene ID: 6647) were first expressed cloned in pET52b(+) vector, producing the constructs pET-SOD1WT and pET-SOD1G93A. In the same way, the human VDAC1 sequence (Gene ID: 7461) was cloned in pET21a(+) vector, producing the construct pET-VDAC1.

SOD1-G93A and SOD1WT were purified by affinity chromatography with Strep-Tactin resin (Qiagen) and VDAC1 was purified by affinity chromatography with Ni-NTA resin (Qiagen).

Both purification procedures were performed following the manufacturers' protocols (Qiagen).

Purified VDAC1, a membrane protein, was refolded in a buffer solution containing 1% Lauryl-dimethyl-amine-N-Oxide (LDAO). The correct folding of recombinant VDAC1 was checked by electrophysiological characterization of its pore-forming features in a planar lipid bilayer (PLB) [Checchetto V. et al., Recombinant human Voltage Dependent Anion selective Channel isoform 3 (hVDAC3) forms pores with a very small conductance. Cell Physiol Biochem (2014) 34(3): 842-853.]. The experimental conditions in the PLB assay were as follows: membrane composition: diphytanoyl-phosphatidylcholine/n-decane; the membrane was bathed from both sides with 1 M KCl in water; the potential applied to the membrane was 10 mV; constant T=25° C.

In these in vitro experiments the interference action of the synthetic peptide NHK1 on the complex VDAC1/SOD1-G93A was evaluated.

Experiment 3—VDAC1 Binding to SOD1-G93A and SOD1WT

Figure 1:
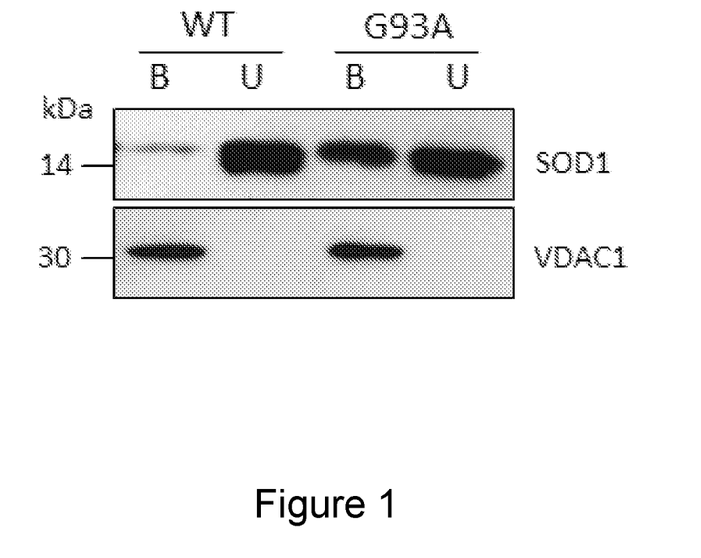
FIG. 1 shows an immunoblotting experiment of an interaction assay performed between magnetic beads bearing VDAC1 molecules interacting with SOD1-G93A (mutant SOD1 G93A) or SOD1WT (wild type phenotype). B: SOD1 bound to VDAC1; U: SOD1 not bound to VDAC1.

The ability of SOD1-G93A and SOD1WT to bind VDAC1 was assayed in the following experimental conditions: 30 µM purified and refolded VDAC1, in its native conformation, were incubated with 50 µL of paramagnetic micro-beads coated with a Ni-NTA resin (nickel-nitrilotriacetic acid) from Qiagen. The resin specifically binds the 6×His-tag located at the C-terminus of VDAC1, coating the beads with the VDAC1 protein itself. VDAC1 bound to the paramagnetic beads interacts with significant affinity with purified human SOD1-G93A, added to the VDAC1-coated micro-beads at a concentration 6.5 µM. In the same conditions there is no binding of SOD1WT to the VDAC1-coated micro-beads (FIG. 1).

This result is in agreement with the literature, i.e. the specific ability of the mutant SOD1, but not of the SOD1WT, to interact with VDAC1 (in vivo) [Israelson A. et al., Misfolded Mutant SOD1 Directly Inhibits VDAC1 Conductance in a Mouse Model of Inherited ALS. Neuron (2010) August 26; 67(4):575-587].

Figure 2:
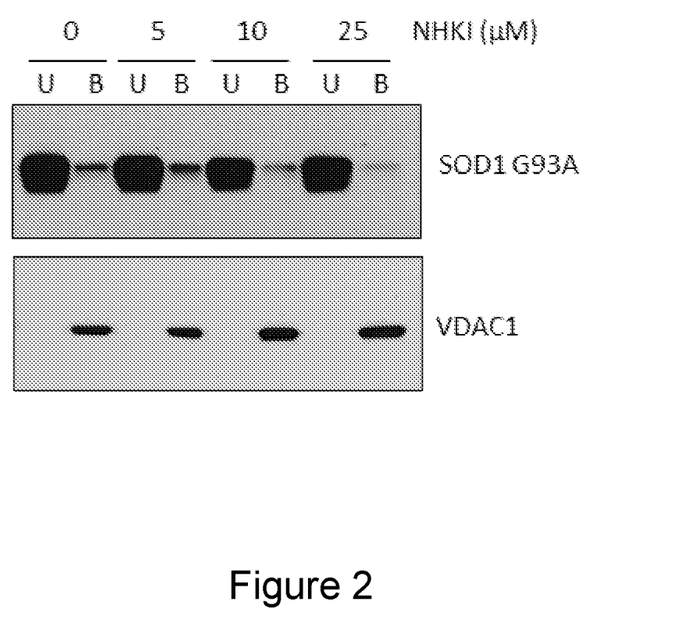
FIG. 2 shows an immunoblotting experiment of an interaction assay performed between magnetic beads bearing VDAC1 molecules interacting with SOD1-G93A in the presence of the peptide NHK1, i.e. the said synthetic peptide object of the invention and with the sequence IAAQLLAYYFT (SEQ. ID NO. 1). B: SOD1 bound to VDAC1; U: SOD1 not bound to VDAC1.

Experiment 4—the Action of Synthetic Peptide NHK1 Against the Complex VDAC1/SOD1-G93A The same experiment described as Experiment 3 was repeated in the presence of raising concentrations of synthetic peptide NHK1 (concentration range from 0 to 25 µM). The peptide was added to VDAC1 at a concentration 30 µM bound to 50 µL of magnetic beads. Next, 6.5 µM SOD1-G93A (or alternatively SOD1WT as a control) were added. The interaction was evaluated by immunoblotting with anti-SOD1 antibody after separation of the bound/unbound fractions. We have found that SOD1-G93A bound to VDAC1 decreased in parallel with the increase of the peptide NHK1 concentration and almost disappeared at the maximal applied peptide concentration (FIG. 2).

In particular, we noticed that SOD1-G93A bound to VDAC1 was 40% reduced in the presence of 10 µM NHK1, and was 80% reduced in the presence of 25 µM NHK1.

Experiment 5—Effect of Synthetic Peptide NHK1 on the Conductance of VDAC1 Porine In a single channel experiment of VDAC1 conductance recording, the pore-forming activity of VDAC1 was observed before and after the addition in the cuvette cis of the synthetic peptide NHK1 (Ben-Hail D, Shoshan-Barmatz V. Reconstitution of purified VDAC1 into a lipid bilayer and recording of channel conductance. Cold Spring Harb Protoc. 2014 Jan. 1; 2014(1):100-5. doi: 10.1101/pdb.prot073148. PubMed PMID: 24371316).

Figure 3:
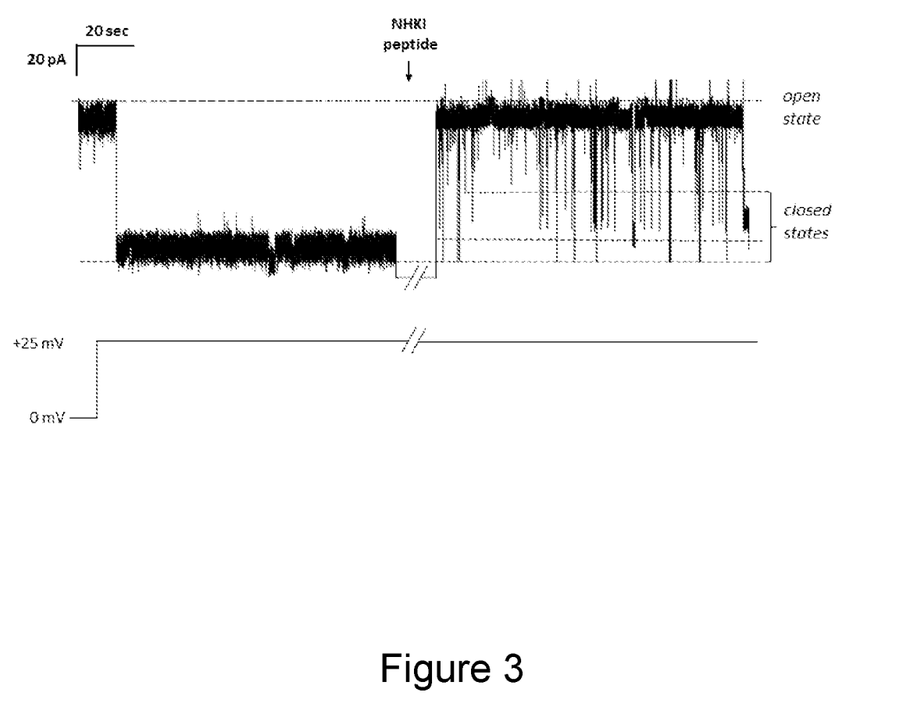
FIG. 3 shows a representative (n=3) electrophysiological trace of VDAC1 incorporated in an artificial planar lipid bilayer with applied voltage +25 mV in 1 M KCl, before and after addition of peptide NHK1. Upon voltage application, VDAC1 conductance is low (closed state); the addition of the said synthetic peptide object of the invention (NHK1) causes a meaningful instability of the channel conductance, that opens and closes with different events of various sizes.

FIG. 3 shows a representative trace of VDAC1 conductance in 1 M KCl at a constant applied voltage +25 mV, before and after the addition of the synthetic peptide NHK1. At the applied voltage, the VDAC1 channel is present in the so-called (partially) "closed" state, as defined in the literature. Following the addition of 15 µM synthetic peptide NHK1, the closed state was destabilized, showing fast fluctuations that range from reaching higher conductance levels and several different closed states.

Experiment 6—Cell Localization of Synthetic Peptide NHK1

The localization of synthetic peptide NHK1 was evaluated by two different fluorescent probes in NSC34-G93A (i.e. NSC34 cell over-expressing the mutant SOD1-G93A) cell.

Experiment 6a—Synthetic Peptide NHK1 Labelled with Biotin

The peptide NHK1 was synthesized modified by the labelling of its N-terminal amino group with a biotin. Following internalization of biotinylated peptide into NSC34-G93A cell driven by the transfection reagent Chariot (Active Motif), the localization of the biotinylated NHK1 peptide was visualized at the fluorescence microscope after the specific interaction of biotin with streptavidin labelled with the fluorescent probe Alexa594 (Molecular Probes-Thermo scientific). In this experiment, 6 µL of the not cytotoxic transfection reagent Chariot were used to allow the uptake in the cell of the biotinylated synthetic peptide (100-400 ng peptide/per well). Chariot is a 2,843 da peptide able to form non covalent complexes with proteins or peptides: in this way it protects the peptide to be uptaken from degradative processes during the transfection process. Once inside the cell, the Chariot-peptide complex dissociates and the peptide can reach its target destination. The uptake is independent from the endosomal pathway, thus the peptide structure is not modified during the internalization.

Chariot experiment was carried out according to the manufacturer's instructions.

Experiment 6b—Synthetic Peptide NHK1 Labelled with Fluorescein Isothiocyanate (FITC)

The peptide NHK1 was synthesized modified by the labelling of its N-terminal amino group with the fluorescent probe Fluorescein isothiocyanate (FITC). Following internalization of the modified peptide into NSC34-G93A cell driven by the transfection reagent Chariot (Active Motif), the localization of the NHK1-FITC peptide was directly visualized at the fluorescence microscope.

In experiment 6a the cellular localization of the peptide NHK1 was obtained by indirect immunofluorescence. In experiment 6b the visualization was obtained by direct immunofluorescence, since FITC is a fluorescent molecule.

Experiments 6a and 6b resulted in overlapping patterns of results: images were acquired by an epifluorescence microscope (Leica DM6000) and showed that both NHK1 peptides (labelled with biotin or with FITC), clearly localized to mitochondria (data not shown in Figures).

Figure 4:
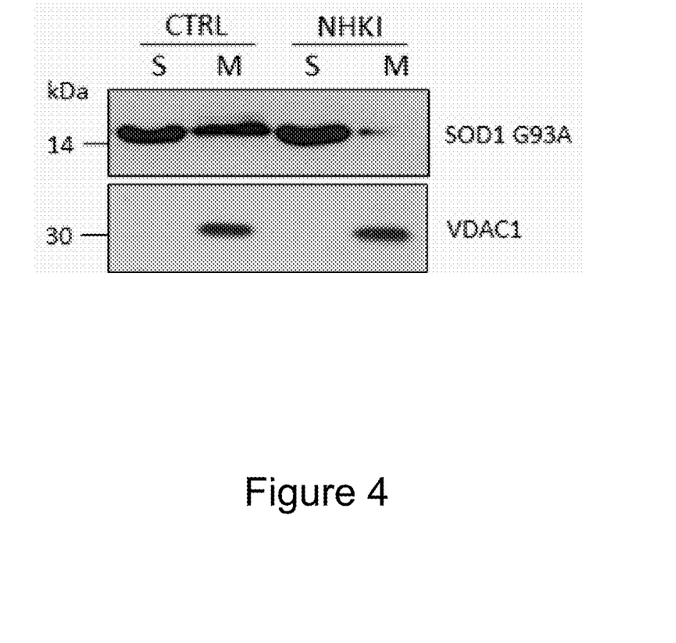
FIG. 4 shows an immunoblotting experiment of an interaction assay performed between mitochondria isolated from NSC34 cells with SOD1-G93A, in the presence of 60 µM peptide NHK1, i.e. the said synthetic peptide object of the invention with the sequence IAAQLLAYYFT (SEQ. ID NO. 1). In the presence of synthetic peptide, SOD1-G93A binds mitochondria at a much lesser extent. S: supernatant fraction, i.e. the fraction containing molecules not bound to mitochondria; M: mitochondrial fraction, i.e. the fraction containing mitochondria and the molecules bound to them.

Experiment 7—the Synthetic Peptide NHK1 Obstructs the Formation of the Complex VDAC1/SOD1-G93A In Vitro The ability of the synthetic peptide NHK1 to obstruct the formation of the complex VDAC1/SOD1-G93A was verified with mitochondria purified from NSC34 cell. In such experiment, 2 µg of SOD1-G93A (or SOD1WT as a control) were incubated with intact mitochondria obtained starting from 10 NSC34 cell. It was noticed that only SOD1-G93A was able to interact with the mitochondrial surface, at variance with SOD1WT, which was unable to interact with mitochondria (FIG. 4). In FIG. 4, "S" indicates the supernatant fraction, containing the SOD1 not bound to mitochondria, while "M" indicates the mitochondrial fraction, i.e. the presence of SOD1-G93A bound to the mitochondria.

In the same experiment, SOD1-G93A bound to mitochondria decreased of about 90% in comparison with the control sample, following the addition of 60 µM NHK1 (FIG. 4).

Experiment 8—the Action of Synthetic Peptide NHK1 in Cellulo

It has been established that protein aggregation is a typical feature of neurodegenerative diseases and, in particular, mutant SOD1 aggregates are toxic and directly associated with the ALS disease.

Figure 5:
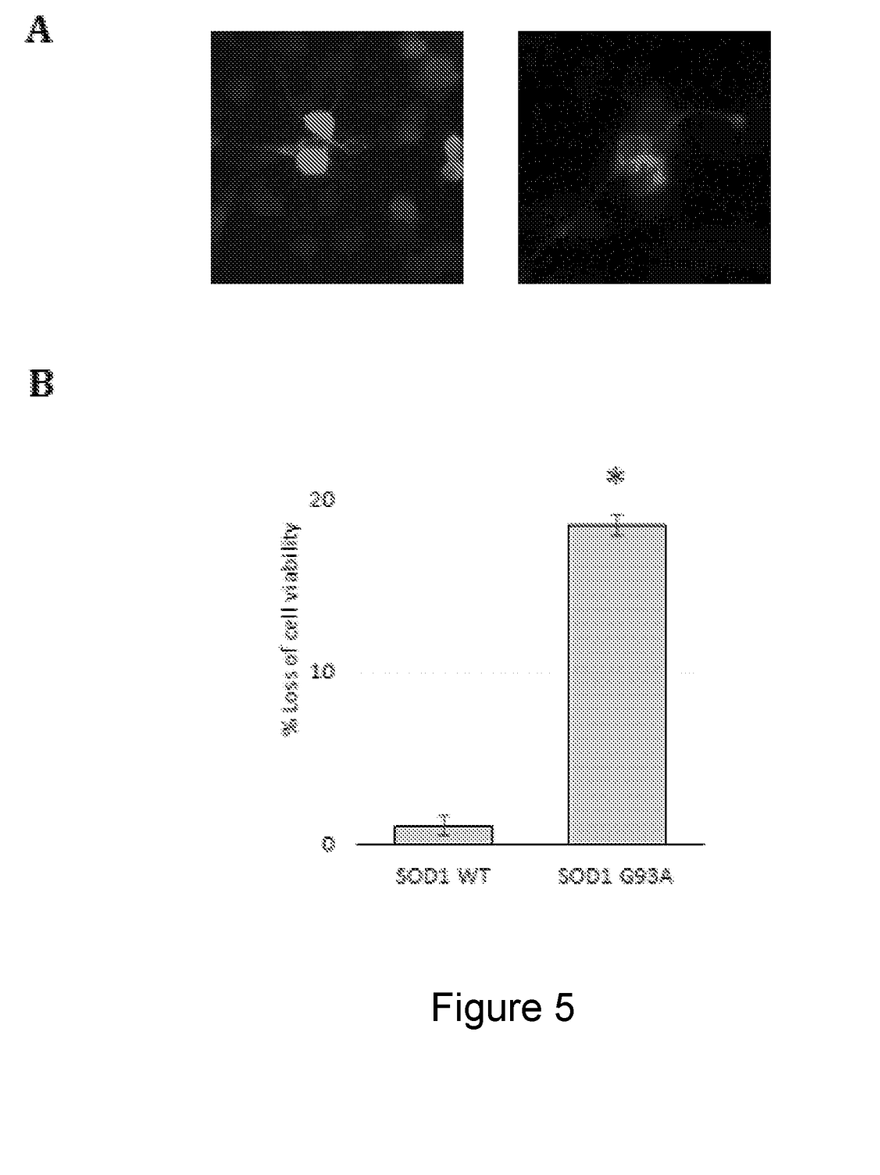
FIG. 5 shows: Panel A) Representative images obtained by confocal microscopy of NSC34 cells over-expressing wt SOD1 (left side) or SOD1-G93A (right side), both fused with eGFP. Only SOD1-G93A induces formation of intracellular aggregates. Panel B) The over-expression of SOD1 impacts on the NSC34 cell vitality. In cell expressing SOD1WT, even at very high levels, there is no special change. On the contrary, in cell expressing the SOD1-G93A, 24 h after transfection, the cell vitality is about 20% reduced (in comparison with control).

Preliminary experiments showed that, in NSC34 cell, the mutated SOD1-G93A induces the formation of intracellular toxic aggregation of proteins. On the contrary, the physiological form of SOD1 (SOD1WT) does not induce such toxic aggregates. FIG. 5A shows representative images, obtained at confocal microscopy, of NSC34 cell where SOD1WT (left side) or SOD1-G93A (right side) fused with eGFP were expressed. Strikingly, only SOD1-G93A expression is associated with the presence of intracellular aggregates, toxic for the cell life.

The action of the NHK1 peptide was assayed in NSC34-G93A cell, following transfection by Lipofectamine 3000 (Invitrogen) with plasmids pCMSmtRed-NHK1 or pCMSmtRed-NHK1-HA, previously defined. With this procedure it is possible to have larger amounts of peptide in the cell than with the direct peptide transfection. Furthermore, it is possible to follow the cell reaction to the transfection for a longer time (even for more days) than with the direct uptake of the peptide with Chariot. We noticed with the MTT assay [Mosmann T., Rapid colorimetric assay for cellular growth and survival: application to proliferation and cytotoxicity assays. J Immunol Methods (1983) 65:55-63.] that NSC34 cell vitality upon transfection with SOD1WT-eGFP does not change in comparison with the same cell not transfected. On the contrary, after 24 hours, NSC34 cell vitality upon transfection with SOD1-G93A-eGFP drops about 20% in comparison with the same cell transfected with SOD1WT-eGFP (FIG. 5B). Data were normalized against NSC34 cell transfected with only the eGFP. The statistical analysis was performed with an ANOVA one-way test. In FIG. 5B, asterisk (*) means that the value has a significativity $P<0.001$ (0.00014005) with respect to SOD1WT. The experiment was performed at least three times with triplicate samples.

The action of NHK1 peptide was evaluated in NSC34 cell expressing SOD1-G93A or SOD1WT.

In this experiment we have indeed co-transfected NSC34 cell with identical concentrations of pET-SOD1G93A (or pET-SOD1WT in the control) together with pCMSmtRed-NHK1 (or pCMSmtRed-NHK1-HA); after 24 hours we performed the vitality MTT test.

The MTT assay is a colorimetric assay aimed to quantify the activity of dehydrogenase enzymes reducing 3-(4,5-dimethyltiazol-2-yl)-2,5-diphenyltetrazolium, yellow, to purple-blue formazan [Mosmann T., Rapid colorimetric assay for cellular growth and survival: application to proliferation and cytotoxicity assays. J Immunol Methods (1983) 65:55-63.]. The reaction happens in mitochondria where the succinate dehydrogenase is active in living cells. The expression of the peptide NHK1 in NSC34-SOD1-G93A allows a vitality recover of about 50% (FIG. 6).

Cells were seeded on 24-wells plates at a density of 80,000 cells/well, incubated for 24 hours and then transiently transfected with plasmid pEGFP-N1 expressing SOD1WT or SOD1-G93A or a mock. The transfection reagent was Lipofectamine 3000 (Life Technologies). In each transfection 1 μg of plasmidic DNA was used. The MTT assay was read after 24 hours incubation. The experiment was repeated in triplicate for at least four times.

The same vitality assay was repeated in the presence of the NHK1 peptide. NSC34 were co-transfected with plasmids pEGFP-N1+pCMS-mtDsRED-NHK1 or pEGFP-N1-SOD1WT+pCMS-mtDsRED-NHK1 (both as controls) or pEGFP-N1-SOD1G93A+pCMS-mtDsRED-NHK1. In each transfection 1 μg of total plasmidic DNA was used. The MTT assay was read after 24 hours incubation. The experiment was repeated in six parallel samples for at least three times. Data were normalized against NSC34 cell transfected with SOD1-G93A-eGFP, which is considered the condition where there is the maximum drop of cell vitality (100%). It is thus concluded that, considering 100% the drop in NSC34 cell vitality due to the mutant SOD1-G93A, the peptide NHK1 is able to reduce the vitality drop by 42% in the same conditions, with a statistical significance of $P<0.01$ (0.003), as indicated in FIG. 6 with the asterisk (*). On the opposite, in control experiments, no significant loss of vitality was observed. In particular, and very important, co-transfection of eGFP with peptide NHK1 shows that the peptide is not toxic at all for the cell (FIG. 6).

Figure 6:
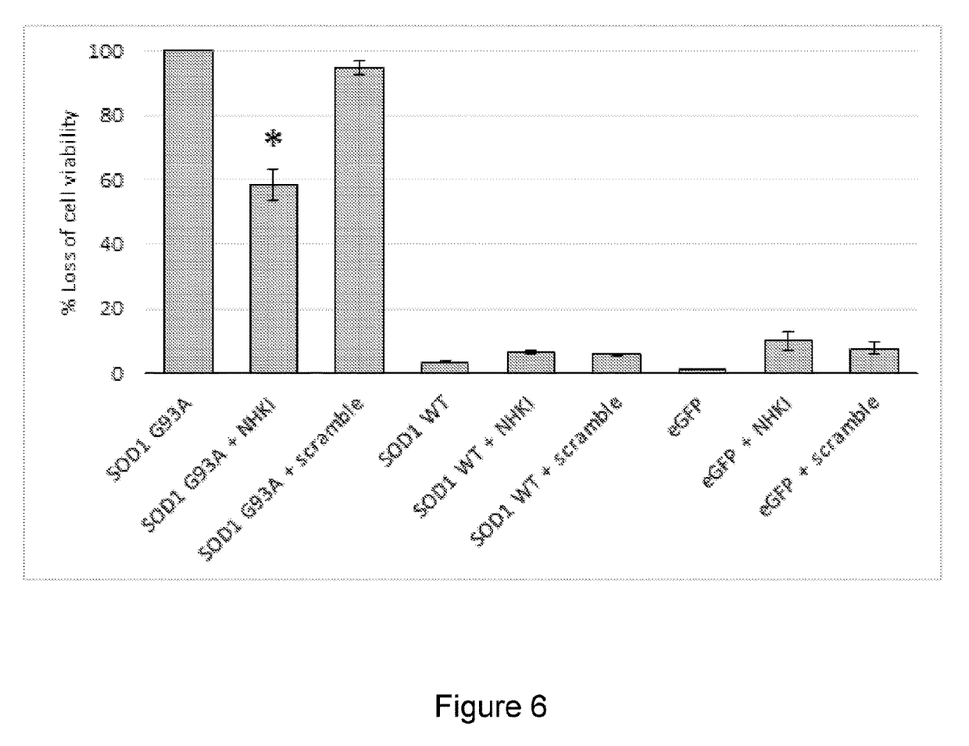
FIG. 6 shows the cell vitality modifications in NSC34-SOD1WT or SOD1-G93A upon expression of the peptide NHK1 or a scramble peptide, used as a control peptide.

No meaningful recovery of cell vitality drop was found when the NSC34-SOD1-G93A cell were co-transfected with a "scramble" peptide as a control ("scramble" in FIG. 6). The scramble peptide has sequence: FAQLTIALAYY (seq. ID NO. 12) (18% sequence identity with the NHK1 peptide seq. ID NO. 1). The statistical analysis was performed with an ANOVA one-way test.

The results from the experiments above described allow us to highlight experimentally the advantages of the present invention, respect to what is known. It has been observed that the synthetic peptide object of the present invention (synthetic peptide NHK1) is able to detach SOD1-G93A bound to VDAC1 or to mitochondria purified from NSC34 cell. Furthermore, experiments in NSC34-SOD1-G93A transgene cell showed that the synthetic peptide offers additional advantages to what is known in the technique and in state of the art: first, it is able to counteract the mortality associated with the expression of mutated SOD1-G93A in motor neurons; it further enhances the cell vitality acting on the mitochondrial function (as it is evident by the MTT assay, which is, at the end, a mitochondria activity assay) [Sanchez N S and Knigsberg M. Using Yeast to Easily Determine Mitochondrial Functionality with 1-(4,5-Dimethylthiazol-2-yl)-3,5-diphenyltetrazolium Bromide (MTT) Assay. Biochem Mol Biol Educ (2006) 34(3):209-212; Kaneko I., Yamada N., Sakuraba Y. et al. Suppression of mitochondrial succinate dehydrogenase, a primary target of beta-amyloid, and its derivative racemized at Ser residue. J Neurochem (1995) 65(6):2585-93.]. A further advantage of synthetic peptide according to the present invention (synthetic peptide NHK1) is its tolerability by the cell, and this can be exploited in treatment of diseases with similar etiological mechanisms as, for example neurodegenerative diseases like ALS.

At the end, a further advantage of the peptide NHK1 and its tolerability by the cell, is in treatment of cancer, since it exherts a pro-apoptotic effect in stable tumor cell (i.e. HeLa cell).

The invention claimed is:

1. Synthetic peptide consisting of amino acid sequence IAAQLLAYYFT (SEQ. ID NO. 1).

2. The synthetic peptide according to claim 1, wherein said synthetic peptide is coupled to a detectable molecule.

3. Pharmaceutical composition comprising the synthetic peptide according to claim 1.

4. A medicament comprising the synthetic peptide according to claim 1.

* * * * *

SEQUENCE LISTING

<160> NUMBER OF SEQ ID NOS: 12

<210> SEQ ID NO 1
<211> LENGTH: 11
<212> TYPE: PRT
<213> ORGANISM: Artificial Sequence
<220> FEATURE:
<223> OTHER INFORMATION: Synthetic peptide (NHK1)

<400> SEQUENCE: 1

Ile Ala Ala Gln Leu Leu Ala Tyr Tyr Phe Thr
1               5                   10

<210> SEQ ID NO 2
<211> LENGTH: 36
<212> TYPE: DNA
<213> ORGANISM: Artificial Sequence
<220> FEATURE:
<223> OTHER INFORMATION: coding sequence for the synthetic peptide
      (NHK1)

<400> SEQUENCE: 2
atcgccgcgc agctcctggc ctattacttc acgtga                          36

<210> SEQ ID NO 3
<211> LENGTH: 45
<212> TYPE: DNA
<213> ORGANISM: Artificial Sequence
<220> FEATURE:
<223> OTHER INFORMATION: oligonucleotide for the production of a plasmid

<400> SEQUENCE: 3
ctagcatgat cgccgcgcag ctcctggcct attacttcac gtgag                45

<210> SEQ ID NO 4
<211> LENGTH: 45
<212> TYPE: DNA
<213> ORGANISM: Artificial Sequence
<220> FEATURE:
<223> OTHER INFORMATION: oligonucletide for the production of a plasmid.
      The sequence is indicated in direction 3'-5'

<400> SEQUENCE: 4
gtactagcgg cgcgtcgagg accggataat gaagtgcact cagct               45

<210> SEQ ID NO 5
<211> LENGTH: 27
<212> TYPE: DNA
<213> ORGANISM: Artificial Sequence
<220> FEATURE:
<223> OTHER INFORMATION: sequence coding for the HA-tag

<400> SEQUENCE: 5
tacccatacg atgttccaga ttacgct                                    27

<210> SEQ ID NO 6
<211> LENGTH: 9
<212> TYPE: PRT
<213> ORGANISM: Artificial Sequence
<220> FEATURE:
<223> OTHER INFORMATION: HA-tag

<400> SEQUENCE: 6

Tyr Pro Tyr Asp Val Pro Asp Tyr Ala
1               5

```
<210> SEQ ID NO 7
<211> LENGTH: 72
<212> TYPE: DNA
<213> ORGANISM: Artificial Sequence
<220> FEATURE:
<223> OTHER INFORMATION: oligonucleotide for the production of a plasmid

<400> SEQUENCE: 7
ctagcatgat cgccgcgcag ctcctggcct attacttcac gtgatacccca tacgatgttc    60 cagattacgc tg                                                          72

<210> SEQ ID NO 8
<211> LENGTH: 72
<212> TYPE: DNA
<213> ORGANISM: Artificial Sequence
<220> FEATURE:
<223> OTHER INFORMATION: oligonucletide for the production of a plasmid.
      The sequence is indicated in direction 3'-5'

<400> SEQUENCE: 8
gtactagcgg cgcgtcgagg accggataat gaagtgcact atgggtatgc tacaaggtct    60
aatgcgacag ct                                                         72

<210> SEQ ID NO 9
<211> LENGTH: 21
<212> TYPE: PRT
<213> ORGANISM: Artificial Sequence
<220> FEATURE:
<223> OTHER INFORMATION: Synthetic peptide

<400> SEQUENCE: 9

Met Ile Ala Ala Gln Leu Leu Ala Tyr Tyr Phe Thr Glu Leu Lys Asp
 1               5                  10                  15

Asp Gln Val Lys Lys
             20

<210> SEQ ID NO 10
<211> LENGTH: 15
<212> TYPE: PRT
<213> ORGANISM: Artificial Sequence
<220> FEATURE:
<223> OTHER INFORMATION: Synthetic peptide

<400> SEQUENCE: 10

Met Ile Ala Ala Gln Leu Leu Ala Tyr Tyr Phe Thr Glu Leu Lys
 1               5                  10                  15

<210> SEQ ID NO 11
<211> LENGTH: 4
<212> TYPE: PRT
<213> ORGANISM: Artificial Sequence
<220> FEATURE:
<223> OTHER INFORMATION: peptide fragment

<400> SEQUENCE: 11

Ala Gln Leu Leu
 1

<210> SEQ ID NO 12
<211> LENGTH: 11
<212> TYPE: PRT
<213> ORGANISM: Artificial Sequence
<220> FEATURE:
<223> OTHER INFORMATION: control peptide "scramble"
```

```
<400> SEQUENCE: 12

Phe Ala Gln Leu Thr Ile Ala Leu Ala Tyr Tyr
1               5                   10
```